United States Patent
Buhr et al.

(10) Patent No.: US 7,223,771 B2
(45) Date of Patent: May 29, 2007

(54) TRICYCLIC IMIDAZOPYRIDINES

(75) Inventors: Wilm Buhr, Constance (DE); Jörg Senn-Bilfinger, Constance (DE)

(73) Assignee: Altana Pharma AG, Constance (DE)

( * ) Notice: Subject to any disclaimer, the term of this patent is extended or adjusted under 35 U.S.C. 154(b) by 176 days.

(21) Appl. No.: 10/485,515

(22) PCT Filed: Jul. 31, 2002

(86) PCT No.: PCT/EP02/08505

§ 371 (c)(1),
(2), (4) Date: Feb. 2, 2004

(87) PCT Pub. No.: WO03/014123

PCT Pub. Date: Feb. 20, 2003

(65) Prior Publication Data

US 2005/0049272 A1    Mar. 3, 2005

(30) Foreign Application Priority Data

Aug. 10, 2001    (EP) .................................. 01119321

(51) Int. Cl.
C07D 221/06    (2006.01)
A61K 31/437    (2006.01)
(52) U.S. Cl. ........................ 514/290; 546/79
(58) Field of Classification Search ............... 546/79; 514/290
See application file for complete search history.

(56) References Cited

U.S. PATENT DOCUMENTS 4,468,400 A * 8/1984 Gold et al. ............... 514/292

FOREIGN PATENT DOCUMENTS

| WO | WO 95/27714 | 10/1995 |
| WO | WO 98/42707 | 10/1998 |
| WO | WO 98/54188 | 12/1998 |
| WO | WO01/72757 | * 10/2001 |

OTHER PUBLICATIONS

Kaminski, J.J. et al. "Antiulcer Agents. 5. Inhibition of Gastric H+/K+-ATPase by Substituted Imidazo [1, 2-a] pyridines and Related Analogues and Its Implication in Modeling the High Affinity Potassium Ion Binding Site of the Gastric Proton Pump Enzyme", J. Med. Chem., vol. 34 pp. 533-541, 1991.
Kaminski, J.J. et al. "Antiulcer Agents. 4. Conformational Considerations and the Antiulcer Activity Substituted Imidazo [1, 2-a] pyridines and Related Analogues", *J.Med.Chem.*, vol. 32 pp. 1686-1700, 1989.

* cited by examiner

*Primary Examiner*—Rita Desai
(74) *Attorney, Agent, or Firm*—The Nath Law Group; Joshua B. Goldberg; Sheldon M. McGee

(57) ABSTRACT

The invention provides compounds of the formula (I), in which the substituents and symbols are as defined in the description. The compounds inhibit the secretion of gastric acid.

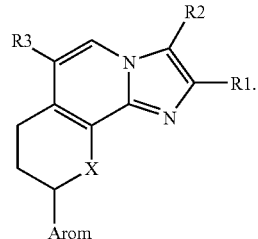

(1)

9 Claims, No Drawings

TRICYCLIC IMIDAZOPYRIDINES

TECHNICAL FIELD

The invention relates to novel compounds which are used in the pharmaceutical industry as active compounds for preparing medicaments.

PRIOR ART

U.S. Pat. No. 4,468,400 describes tricyclic imidazo[1,2-a]pyridines having different ring systems fused to the imidazopyridine skeleton, which compounds are said to be suitable for treating peptide ulcer disorders. The International Patent Applications WO95/27714, WO98/42707, WO98/54188, WO00/17200, WO00/26217 and WO 00/63211 disclose tricyclic imidazopyridine derivatives having a very specific substitution pattern, which compounds are likewise said to be suitable for treating gastrointestinal disorders.—Kaminski et al., J. Med. Chem. 1991, 34, 533–541 and 1997, 40, 427–436 describe the synthesis of imidazo[1,2-a]pyridines and their use as antiulcer agents.

DESCRIPTION OF THE INVENTION

The invention provides compounds of the formula 1

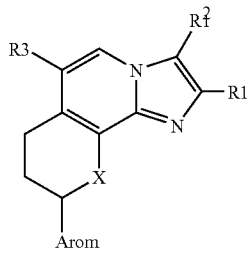

(1)

where
R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl,
R2 is hydrogen, 1–4C-alkyl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl,
R3 is hydroxy-1–4C-alkyl, 1–4C-alkoxy-1–4C-alkyl, 1–4C-alkoxy-1–4C-alkoxy-1–4C-alkyl, 1–4C-alkoxycarbonyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together and including the nitrogen atom to which they are attached form a pyrrolidino, piperidino or morpholino radical,
Arom is a R4-, R5-, R6- and R7-substituted mono- or bicyclic aromatic radical selected from the group consisting of phenyl, naphthyl, pyrrolyl, pyrazolyl, imidazolyl, 1,2,3-triazolyl, indolyl, benzimidazolyl, furanyl (furyl), benzofuranyl (benzofuryl), thiophenyl (thienyl), benzothiophenyl (benzothienyl), thiazolyl, isoxazolyl, pyridinyl, pyrimidinyl, quinolinyl and isoquinolinyl,
where
R4 is hydrogen, 1–4C-alkyl, hydroxy-1–4C-alkyl, 1–4C-alkoxy, 2–4C-alkenyloxy, 1–4C-alkylcarbonyl, carboxyl, 1–4C-alkoxycarbonyl, carboxy-1–4C-alkyl, 1–4C-alkoxycarbonyl-1–4C-alkyl, halogen, hydroxyl, aryl, aryl-1–4C-alkyl, aryloxy, aryl-1–4C-alkoxy, trifluoromethyl, nitro, amino, mono- or di-1–4C-alkylamino, 1–4C-alkylcarbonylamino, 1–4C-alkoxycarbonylamino, 1–4C-alkoxy-1–4C-alkoxycarbonylamino or sulfonyl,
R5 is hydrogen, 1–4C-alkyl, 1–4C-alkoxy, 1–4C-alkoxycarbonyl, halogen, trifluoromethyl or hydroxyl,
R6 is hydrogen, 1–4C-alkyl or halogen and
R7 is hydrogen, 1–4C-alkyl or halogen,
where
aryl is phenyl or substituted phenyl having one, two or three identical or different substituents from the group consisting of 1–4C-alkyl, 1–4C-alkoxy, carboxyl, 1–4C-alkoxycarbonyl, halogen, trifluoromethyl, nitro, trifluoromethoxy, hydroxyl and cyano,
X is O (oxygen) or NH,
and their salts.

1–4C-Alkyl denotes straight-chain or branched alkyl radicals having 1 to 4 carbon atoms. Examples which may be mentioned are the butyl, isobutyl, sec-butyl, tert-butyl, propyl, isopropyl, ethyl and methyl radicals.

3–7C-Cycloalkyl denotes cyclopropyl, cyclobutyl, cyclopentyl, cyclohexyl and cycloheptyl, among which cyclopropyl, cyclobutyl and cyclopentyl are preferred.

3–7C-Cycloalkyl-1–4C-alkyl denotes one of the abovementioned 1–4C-alkyl radicals which is substituted by one of the abovementioned 3–7C-cycloalkyl radicals. Examples which may be mentioned are the cyclopropylmethyl, the cyclohexylmethyl and the cyclohexylethyl radicals.

1–4C-Alkoxy denotes radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

1–4C-Alkoxy-1–4C-alkyl denotes one of the abovementioned 1–4C-alkyl radicals which is substituted by one of the abovementioned 1–4C-alkoxy radicals. Examples which may be mentioned are the methoxymethyl, the methoxyethyl and the butoxyethyl radicals.

1–4C-Alkoxycarbonyl (—CO-1–4C-alkoxy) denotes a carbonyl group to which is attached one of the abovementioned 1–4C-alkoxy radicals. Examples which may be mentioned are the methoxycarbonyl ($CH_3O$—C(O)—) and the ethoxycarbonyl ($CH_3CH_2O$—C(O)) radicals.

2–4C-Alkenyl denotes straight-chain or branched alkenyl radicals having 2 to 4 carbon atoms. Examples which may be mentioned are the 2-butenyl, 3-butenyl, 1-propenyl and the 2-propenyl (allyl) radicals.

2–4C-Alkynyl denotes straight-chain or branched alkynyl radicals having 2 to 4 carbon atoms. Examples which may be mentioned are the 2-butynyl, the 3-butynyl and, preferably, the 2-propynyl (propargyl radicals).

Fluoro-1–4C-alkyl denotes one of the abovementioned 1–4C-alkyl radicals which is substituted by one or more fluorine atoms. An example which may be mentioned is the trifluoromethyl radical.

Hydroxy-1–4C-alkyl denotes abovementioned 1–4C-alkyl radicals which are substituted by a hydroxyl group. Examples which may be mentioned are the hydroxymethyl, the 2-hydroxyethyl and the 3-hydroxypropyl radicals.

For the purpose of the invention, halogen is bromine, chlorine and fluorine.

1–4C-Alkoxy-1–4C-alkoxy denotes one of the abovementioned 1–4C-alkoxy radicals which is substituted by a further 1–4C-alkoxy radical. Examples which may be mentioned are the radicals 2-(methoxy)ethoxy (CH$_3$—O—CH$_2$—CH$_2$—O—) and 2-(ethoxy)ethoxy (CH$_3$—CH$_2$—O—CH$_2$—CH$_2$—O—).

1–4C-Alkoxy-1–4C-alkoxy-1–4C-alkyl denotes one of the abovementioned 1–4C-alkoxy-1–4C-alkyl radicals which is substituted by one of the abovementioned 1–4C-alkoxy radicals. An example which may be mentioned is the radical 2-(methoxy)ethoxymethyl (CH$_3$—O—CH$_2$—CH$_2$—O—CH$_2$—).

Fluoro-1–4C-alkoxy-1–4C-alkyl denotes one of the abovementioned 1–4C-alkyl radicals which is substituted by a fluoro-1–4C-alkoxy radical. Here, fluoro-1–4C-alkoxy denotes one of the abovementioned 1–4C-alkoxy radicals which is fully or predominantly substituted by fluorine. Examples of fully or predominantly fluorine-substituted 1–4C-alkoxy which may be mentioned are the 1,1,1,3,3,3-hexafluoro-2-propoxy, the 2-trifluoromethyl-2-propoxy, the 1,1,1-trifluoro-2-propoxy, the perfluoro-tert-butoxy, the 2,2,3,3,4,4,4-heptafluoro-1-butoxy, the 4,4,4-trifluoro-1-butoxy, the 2,2,3,3,3-penta-fluoropropoxy, the perfluoroethoxy, the 1,2,2-trifluoroethoxy, in particular the 1,1,2,2-tetrafluoroethoxy, the 2,2,2-trifluoroethoxy, the trifluoromethoxy and preferably the difluoromethoxy radicals.

–7C-Alkyl denotes straight-chain or branched alkyl radicals having 1 to 7 carbon atoms. Examples which may be mentioned are the heptyl, isoheptyl-(5methylhexyl), hexyl, isohexyl-(4-methylpentyl), neohexyl-(3,3-dimethylbutyl), pentyl, isopentyl-(3-methylbutyl), neopentyl-(2,2-dimethylpropyl), butyl, isobutyl, sec-butyl, tert-butyl, propyl, isopropyl, ethyl and methyl radicals.

1–4C-Alkylcarbonyl denotes a radical which, in addition to the carbonyl group, contains one of the abovementioned 1–4C-alkyl radicals. An example which may be mentioned is the acetyl radical.

Carboxy-1–4C-alkyl denotes, for example, the carboxymethyl (—CH$_2$COOH) or the carboxyethyl (—CH$_2$CH$_2$COOH) radical.

1–4C-Alkoxycarbonyl-1–4C-alkyl denotes one of the abovementioned 1–4C-alkyl radicals which is substituted by one of the abovementioned 1–4C-alkoxycarbonyl radicals. An example which may be mentioned is the ethoxycarbonylmethyl (CH$_3$CH$_2$OC(O)CH$_2$—) radical.

Di-1–4C-alkylamino denotes an amino radical which is substituted by two identical or different of the abovementioned 1–4C-alkyl radicals. Examples which may be mentioned are the dimethylamino, the diethylamino and the diisopropylamino radicals.

1–4C-Alkoxycarbonylamino denotes an amino radical which is substituted by one of the abovementioned 1–4C-alkoxycarbonyl radicals. Examples which may be mentioned are the ethoxycarbonylamino and the methoxycarbonylamino radicals.

1–4C-Alkoxy-1–4C-alkoxycarbonyl denotes a carbonyl group to which one of the abovementioned 1–4C-alkoxy-1–4C-alkoxy radicals is attached. Examples which may be mentioned are the 2-(methoxy)ethoxycarbonyl (CH$_3$—O—CH$_2$CH$_2$—O—CO—) and the 2-(ethoxy)ethoxycarbonyl (CH$_3$CH$_2$—O—CH$_2$CH$_2$—O—CO—) radicals.

1–4C-Alkoxy-1–4C-alkoxycarbonylamino denotes an amino radical which is substituted by one of the abovementioned 1–4C-alkoxy-1–4C-alkoxycarbonyl radicals. Examples which may be mentioned are the 2-(methoxy)ethoxycarbonylamino and the 2-(ethoxy)ethoxycarbonylamino radicals.

2–4C-Alkenyloxy denotes a radical which, in addition to the oxygen atom, contains a 2–4C-alkenyl radical. An example which may be mentioned is the allyloxy radical.

Aryl-1–4C-alkyl denotes an aryl-substituted 1–4C-alkyl radical. An example which may be mentioned is the benzyl radical.

Aryl-1–4C-alkoxy denotes an aryl-substituted 1–4C-alkoxy radical. An example which may be mentioned is the benzyloxy radical.

Mono- or di-1–4C-alkylamino radicals contain, in addition to the nitrogen atom, one or two of the abovementioned 1–4C-alkyl radicals. Preference is given to di-1–4C-alkylamino and in particular to dimethyl-, diethyl- or diisopropylamino.

1–4C-Alkylcarbonylamino denotes an amino group to which a 1–4C-alkylcarbonyl radical is attached. Examples which may be mentioned are the propionylamino (C$_3$H$_7$C(O)NH—) and the acetylamino (acetamido, CH$_3$C(O)NH—) radicals.

Radicals Arom which may be mentioned are, for example, the following substituents: 4-acetoxyphenyl, 4-acetamidophenyl, 2-methoxyphenyl, 3-methoxyphenyl, 4-methoxyphenyl, 3-benzyloxyphenyl, 4-benzyloxyphenyl, 3-benzyloxy-4-methoxyphenyl, 4-benzyloxy-3-methoxyphenyl, 3,5-bis-(trifluoromethyl)phenyl, 4-butoxyphenyl, 2-chlorophenyl, 3-chlorophenyl, 4-chlorophenyl, 2-chloro-6-fluorophenyl, 3-chloro-4-fluorophenyl, 2-chloro-5-nitrophenyl, 4-chloro-3-nitrophenyl, 3-(4-chloro-phenoxy)phenyl, 2,4-dichlorophenyl, 3,4-difluorophenyl, 2,4-dihydroxyphenyl, 2,6-dimethoxyphenyl, 3,4-dimethoxy-5-hydroxyphenyl, 2,5-dimethylphenyl, 3-ethoxy-4-hydroxyphenyl, 2-fluorophenyl, 4-fluorophenyl, 4-hydroxyphenyl, 2-hydroxy-5-nitrophenyl, 3-methoxy-2-nitrophenyl, 3-nitrophenyl, 2,3,5-trichlorophenyl, 2,4,6-trihydroxyphenyl, 2,3,4-trimethoxyphenyl, 2-hydroxy-1-naphthyl, 2-methoxy-1-naphthyl, 4-methoxy-1-naphthyl, 1-methyl-2-pyrrolyl, 2-pyrrolyl, 3-methyl-2-pyrrolyl, 3,4-dimethyl-2-pyrrolyl, 4-(2-methoxycarbonylethyl)-3-methyl-2-pyrrolyl, 5-ethoxycarbonyl-2,4-dimethyl-3-pyrrolyl, 3,4-dibromo-5-methyl-2-pyrrolyl, 2,5-dimethyl-1-phenyl-3-pyrrolyl, 5-carboxy-3-ethyl-4-methyl-2-pyrrolyl, 3,5-dimethyl-2-pyrrolyl, 2,5- dimethyl-1-(4-trifluoromethylphenyl)-3-pyrrolyl, 1-(2,6-dichloro-4-trifluoromethylphenyl)-2-pyrrolyl, 1-(2-nitrobenzyl)-2-pyrrolyl, 1-(2-fluorophenyl)-2-pyrrolyl, 1-(4-fluoromethoxyphenyl)-2-pyrrolyl, 1-(2-nitrobenzyl)-2-pyrrolyl, 1-(4-ethoxycarbonyl)-2,5-dimethyl-3-pyrrolyl, 5-chloro-1,3-dimethyl-4-pyrazolyl, 5-chloro-1-methyl-3-trifluoromethyl-4-pyrazolyl, 1-(4-chloro-benzyl)-5-pyrazolyl, 1,3-dimethyl-5-(4-chlorophenoxy)-4-pyrazolyl, 1-methyl-3-trifluoromethyl-5-(3-trifluoromethylphenoxy)-4-pyrazolyl, 4-methoxycarbonyl-1-(2,6-dichlorophenyl)-5-pyrazolyl, 5-allyloxy-1-methyl-3-trifluoromethyl-4-pyrazolyl, 5-chloro-1-phenyl-3-trifluoromethyl-4-pyrazolyl, 3,5-dimethyl-1-phenyl-4-imidazolyl, 4-bromo-1-methyl-5-imidazolyl, 2-butylimidazolyl, 1-phenyl-1,2,3-triazol-4-yl, 3-indolyl, 4-indolyl, 7-indolyl, 5-methoxy-3-indolyl, 5-benzyloxy-3-indolyl, 1-benzyl-3-indolyl, 2-(4-chlorophenyl)-3-indolyl, 7-benzyloxy-3-indolyl, 6-benzyloxy-3-indolyl, 2-methyl-5-nitro-3-indolyl, 4,5,6,7-tetrafluoro-3-indolyl, 1-(3,5-difluorobenzyl)-3-indolyl, 1-methyl-2-(4-trifluorophenoxy)-3-indolyl, 1-methyl-2-benzimidazolyl, 5-nitro-2-furyl, 5-hydroxymethyl-2-furyl, 2-furyl, 3-furyl, 5-(2-nitro-4-trifluoromethylphenyl)-2-furyl, 4-ethoxycarbonyl-5-methyl-2-furyl, 5-(2-trifluoromethoxyphenyl)-2-furyl, 5-(4-methoxy-2-nitrophenyl)-2-furyl, 4-bromo-2-furyl, 5-dimethylamino-2-furyl, 5-bromo-2-furyl, 5-sulfo-2-furyl, 2-benzofuryl, 2-thienyl, 3-thienyl, 3-methyl-2-thienyl, 4-bromo-2-thienyl, 5-bromo-2-thienyl, 5-nitro-2-thienyl, 5-methyl-2-thienyl, 5-(4-methoxyphenyl)-2-thienyl, 4-methyl-2-thienyl, 3-phenoxy-2-thienyl, 5-carboxy-2-thienyl, 2,5-dichloro-3-thienyl, 3-methoxy-2-thienyl, 2-benzothienyl, 3-methyl-2-benzothienyl, 2-bromo-5-chloro-3-benzothienyl, 2-thiazolyl, 2-amino-4-chloro-5-thiazolyl, 2,4-dichloro-5-thiazolyl, 2-diethylamino-5-thiazolyl, 3-methyl-4-nitro-5-isoxazolyl, 2-pyridyl, 3-pyridyl, 4-pyridyl, 6-methyl-2-pyridyl, 3-hydroxy-5-hydroxymethyl-2-methyl-4-pyridyl, 2,6-dichloro-4-pyridyl, 3-chloro-5-trifluoromethyl-2-pyridyl, 4,6-dimethyl-2-pyridyl, 4-(4-chlorophenyl)-3-pyridyl, 2-chloro-5-methoxycarbonyl-6-methyl-4-phenyl-3-pyridyl, 2-chloro-3-pyridyl, 6-(3-trifluoromethylphenoxy)-3-pyridyl, 2-(4-chlorophenoxy)-3-pyridyl, 2,4-dimethoxy-5-pyrimidine, 2-quinolinyl, 3-quinolinyl, 4-quinolinyl, 2-chloro-3-quinolinyl, 2-chloro-6-methoxy-3-quinolinyl, 8-hydroxy-2-quinolinyl and 4-isoquinolinyl.

Suitable salts of compounds of the formula 1 are—depending on the substitution—in particular all acid addition salts. Particular mention may be made of the pharmacologically acceptable salts of the inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in the salt preparation in an equimolar ratio or in a ratio differing therefrom, depending on whether the acid is a mono- or polybasic acid and on which salt is desired.

Pharmacologically unacceptable salts, which can be initially obtained, for example, as process products in the preparation of the compounds according to the invention on an industrial scale, are converted into pharmacologically acceptable salts by processes known to the person skilled in the art.

It is known to the person skilled in the art that the compounds according to the invention and their salts can, for example when they are isolated in crystalline form, comprise varying amounts of solvents. The invention therefore also embraces all solvates and, in particular, all hydrates of the compounds of the formula 1, and all solvates and, in particular, all hydrates of the salts of the compounds of the formula 1.

The compounds of the formula 1 have at least one center of chirality in the skeleton. The invention thus provides all feasible enantiomers in any mixing ratio, including the pure enantiomers, which are the preferred subject matter of the invention.

Particular mention may be made of those compounds of the formula 1, where

R1 is hydrogen, 1–4C-alkyl, 3–7C-cycloalkyl, 1–4C-alkoxy-1–4C-alkyl, 2–4C-alkynyl or fluoro-1–4C-alkyl R2 is hydrogen, 1–4C-alkyl, halogen, 2–4C-alkenyl, 2–4C-alkynyl or fluoro-1–4-C-alkyl R3 is hydroxy-1–4C-alkyl, 1–4C-alkoxy-1–4C-alkyl, 1–4C-alkoxy-1–4C-alkoxy-1–4C-alkyl, 1–4C-alkoxycarbonyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together and including the nitrogen atom to which they are attached are a pyrrolidino, piperidino or morpholino radical, Arom is a R4-, R5-, R6- and R7-substituted mono- or bicyclic aromatic radical selected from the group consisting of phenyl, furanyl (furyl) and thiophenyl (thienyl), where R4 is hydrogen, 1–4C-alkyl, hydroxy-1–4C-alkyl, 1–4C-alkoxy, 1–4-alkylcarbonyl, carboxyl, 1–4C-alkoxycarbonyl, halogen, hydroxyl, trifluoromethyl, 1–4C-alkylcarbonylamino, 1–4C-alkoxycarbonylamino, 1–4C-alkoxy-1–4C-alkoxycarbonylamino or sulfonyl, R5 is hydrogen, 1–4C-alkyl, 1–4C-alkoxy, 1–4C-alkoxycarbonyl, halogen, trifluoromethyl or hydroxyl, R6 is hydrogen or 1–4C-alkyl and R7 is hydrogen, X is O (oxygen) or NH, and their salts.

Compounds which are to be emphasized are those compounds of the formula 1 where

R1 is 1–4C-alkyl,

R2 is 1–4C-alkyl, halogen or fluoro-1–4C-alkyl,

R3 is hydroxy-1–4C-alkyl, 1–4C-alkoxy-1–4C-alkyl, 1–4C-alkoxy-1–4C-alkoxy-1–4C-alkyl, 1–4C-alkoxycarbonyl or the radical —CO—NR31R32, where
R31 is hydrogen, 1–4C-alkyl, hydroxy-1–4C-alkyl or 1–4C-alkoxy-1–4C-alkyl and
R32 is 1–4C-alkyl, hydroxy-1–4C-alkyl or 1–4C-alkoxy-1–4C-alkyl,
or where
R31 and R32 together and including the nitrogen atom to which they are attached are a pyrrolidino, piperidino or morpholino radical,
Arom is R4-, R5-, R6- and R7-substituted phenyl,
where
R4 is hydrogen or 1–4C-alkyl,
R5 is hydrogen or 1–4C-alkyl,
R6 is hydrogen or 1–4C-alkyl and
R7 is hydrogen,
X is O (oxygen) or NH,
and their salts.

Particular emphasis is given to compounds of the formula 1 where
R1 is methyl,
R2 is methyl, chlorine or difluoromethyl,
R3 is hydroxymethyl, methoxymethyl, methoxyethoxymethyl, 1–4C-alkoxycarbonyl or the radical —CO—NR31R32,
where
R31 is methyl or ethyl and
R32 is methyl or ethyl,
or where
R31 and R32 together and including the nitrogen atom to which they are attached are a morpholino radical,
Arom is phenyl, 2-methylphenyl, 2-isopropylphenyl, 2,6-dimethylphenyl, 2,6-diisopropylphenyl, 2,4,6-trimethylphenyl or 2,4,6-triisopropylphenyl and
X is O (oxygen) or NH,
and their salts.

Particular emphasis is also given to compounds of the formula 1 where
R1 is 1–4C-alkyl,
R2 is 1–4C-alkyl,
R3 is 1–4C-alkoxycarbonyl or the radical —CO—NR31R32,
where
R31 is 1–4C-alkyl and
R32 is 1–4C-alkyl,
Arom is phenyl and
X is O (oxygen),
and their salts.

Particular emphasis is additionally given to compounds of the formula 1 where
R1 is 1–4C-alkyl,
R2 is 1–4C-alkyl,
R3 is 1–4C-alkoxycarbonyl or the radical —CO—NR31R32,
where
R31 is 1–4C-alkyl and
R32 is 1–4C-alkyl,
Arom is phenyl or 2-methyl-6-ethylphenyl and
X is O (oxygen),
and their salts.

Exemplary compounds according to the invention are for example 2,3-dimethyl-9-phenyl-7H-8,9-dihydro-pyrano[2,3-c]-imidazo[1,2-a]pyridine-6-(N,N-dimethyl)carbamide, 2,3-dimethyl-9-(2-ethyl-6-methyl-phenyl-7H-8,9-dihydro-pyrano[2,3-c]imidazo[1,2-a]pyridine-6-(N,N-dimethyl)carbamide, 2,3-dimethyl-9-(2-ethyl-6-methyl-phenyl)-7H-8,9-dihydro-pyrano[2,3-c]-imidazo[1,2-a]pyridine-6-(N,N-diethyl)carbamide, 2,3-dimethyl-9-phenyl-7H-8,9-dihydro-pyrano[2,3-c]-imidazo[1,2-a]pyridine-6-(N,N-diethyl)carbamide, ethyl 2,3-dimethyl-9-phenyl-7H-8,9-dihydro-pyrano[2,3-c]-imidazo[1,2-a]pyridine-6-carboxylate, methyl 2,3-dimethyl-9-phenyl-7H-8,9-dihydro-pyrano[2,3-c]-imidazo[1,2-a]pyridine-6-carboxylate, ethyl 2,3-dimethyl-9-(2-ethyl-6-methyl-phenyl)-7H-8,9-dihydro-pyrano[2,3-c]-imidazo[1,2-a]pyridine-6-carboxylate and methyl 2,3-dimethyl-9-(2-ethyl-6-methyl-phenyl)-7H-8,9-dihydro-pyrano[2,3-c]-imidazo[1,2-a]pyridine-6-carboxylate, and the salts of these compounds.

The compounds according to the invention can be prepared as described in an exemplary manner in the examples below, or starting from appropriate starting materials using analogous process steps (see, for example, U.S. Pat. No. 4,468,400 or WO 95/27714), or as illustrated quite generally in the schemes below.

Scheme 1: Preparation of compounds 1 where X = O, with any substituents R1, R2, R3 and Arom

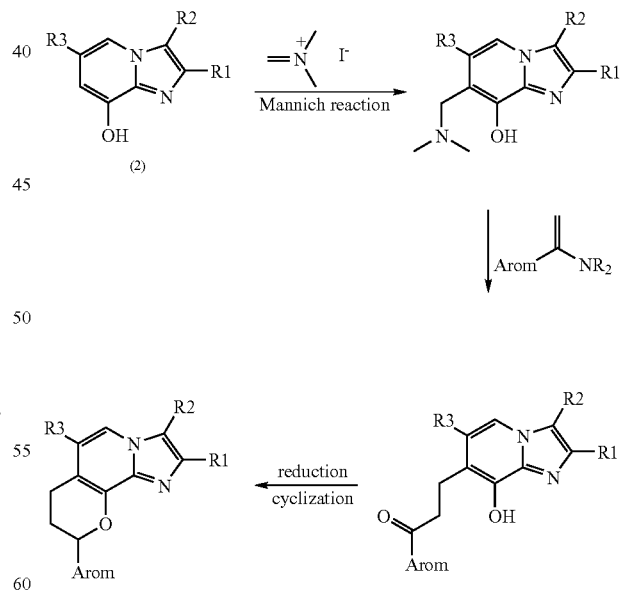

The individual process steps are carried out in a manner known per se to the person skilled in the art, for example as described in more detail in WO 95/27714.

Compounds of the formula 1 where X=NH can be obtained according to Scheme 2 below:

Scheme 2: Preparation of compounds 1 where X = NH, with any substituents R1, R2, R3 and Arom
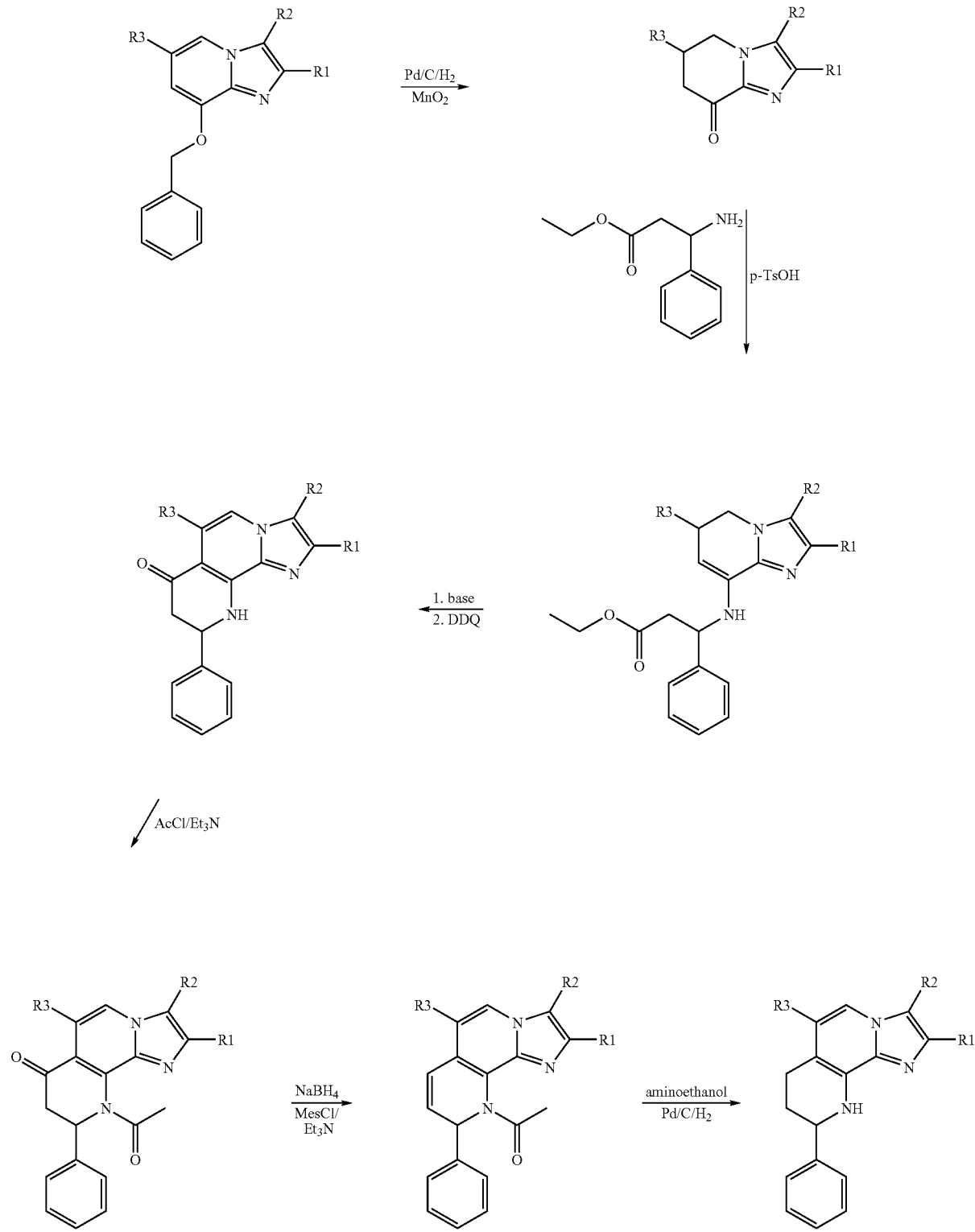

The starting materials shown in Schemes 1 and 2 can be prepared, for example, according to the procedures illustrated in Scheme 3 below.
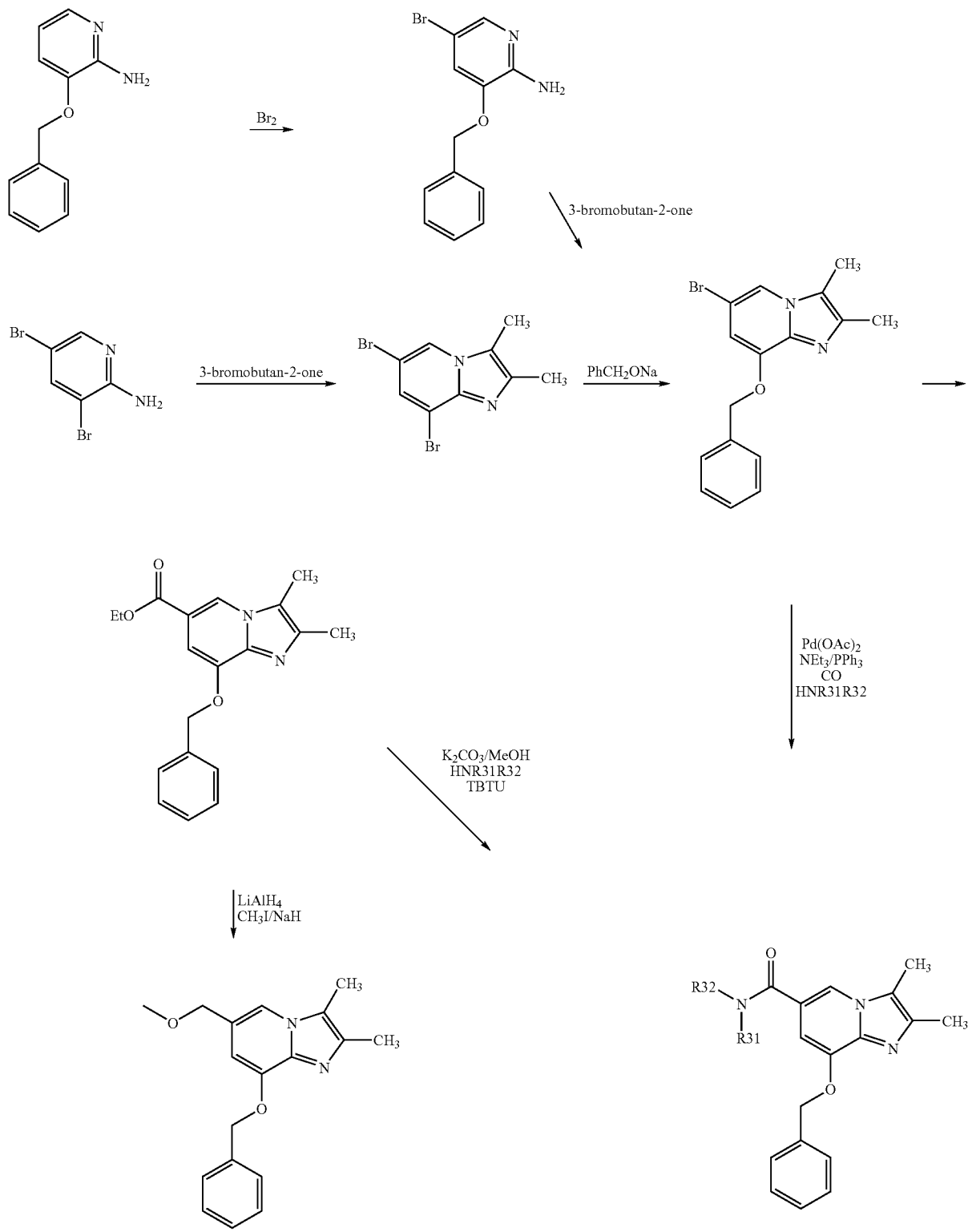
Scheme 3: Exemplary preparation of the starting materials required for Schemes 1 and 2, here with R1, R2 = methyl and various substituents R3.

The preparation of the 8-benzyloxy-6-bromoimidazopyridines is carried out in a manner known per se to the person skilled in the art. Conversion of the bromine atom into an ethyl ester radical can be effected by various routes, for example using the Heck carbonylation (with Pd(II), carbon monoxide and ethanol) or by metallation in the 6-position (with lithium or magnesium) and subsequent Grignard reaction. Metallation also offers the option to introduce other desired groups R3 into position 6. Starting from the ester group, it is possible to introduce further desired groups R3 into position 6, for example hydroxy-1–4C-alkyl radicals (in particular the hydroxymethyl radical), by reducing the ester radical with lithium aluminum hydride, or 1–4C-alkoxy-1–4C-alkyl radicals (in particular 1–4C-alkoxymethyl radicals) by subsequent etherification as illustrated in Scheme 3.

To obtain the compounds of the formula 2, the 8-benzyloxy compounds prepared according to Scheme 3 have to be debenzylated. The debenzylation/reduction of these 8-benzyloxy compounds is likewise carried out in a manner known per se, for example using hydrogen/Pd(0).

If compounds of the formula 2 where R3=—CO—NR31R32 are desired, it is possible to carry out a corresponding derivatization in a manner known per se (conversion of an ester into an amide or direct introduction of the amide radical starting with the 6-bromo compound).

Starting materials with various substituents R1 and R2 are known, or they can be prepared in a known manner, analogously to known compounds, for example based on Scheme 3. Alternatively, derivatizations can also be carried out at the stage of the compounds 1. Thus, using compounds where R2=H, it is possible to prepare, for example, compounds where R2=CH$_2$OH (by Vilsmaier reaction and subsequent reduction), where R2=Cl or Br (by chlorination or bromination), where R2=propynyl (from the corresponding bromine compound using the Sonogashira reaction) or where R2=alkoxycarbonyl (from the corresponding bromine compound by Heck carbonylation).

The examples below serve to illustrate the invention in more detail without limiting it. Further compounds of the formula 1 whose preparation is not described explicitly can likewise be prepared in an analogous manner or in a manner known per se to the person skilled in the art, using customary process techniques. The compounds named expressly as examples, and the salts of these compounds, are preferred subject matter of the invention. The abbreviation min stands for minute(s), h stands for hour(s) and m.p. stands for melting point.

EXAMPLES

End Products 1. 2,3-Dimethyl-9-phenyl-7H-8,9-dihydro-pyrano-[2,3-c]-N-(diethyl)imidazo[1,2-a]pyridine-6-carboxamide At 25° C., 3 ml of boron trifluoride etherate are added dropwise with stirring to a solution of 1.00 g (2.53 mmol) of 2,3-dimethyl-8-hydroxy-7-((3-phenyl-3-hydroxy)propanyl)-N-(diethyl)imidazo[1,2-a]-pyridin-6-carboxamide in dichloromethane. The reaction mixture is stirred at 25° C. for another 4 h and then poured into saturated NaHCO$_3$ solution and extracted repeatedly with dichloromethane. The combined organic phases are concentrated under reduced pressure. The resulting crude product is separated by column chromatography (dichloromethane/methanol: 13/1) and purified. This gives 0.90 g (2.38 mmol) of the title compound as a colorless foam. $^1$H-NMR (200 MHz, [D$_6$]-DMSO, 100° C.): δ=1.19 (t, 6 H), 2.17–2.30 (m, 2 H) 2.35 (s, 3 H), 2.43 (s, 3 H), 2.55–2.69 (m, 1 H), 2.77–2.93 (m, 1 H), 3.42 (dd, 4 H), 5.35 (dd, 1 H), 7.43–7.57 (m, 5 H), 7.73 (s, 1 H).

2. Ethyl 2,3-dimethyl-9-phenyl-7H-8,9-dihydropyrano[2,3-c]-imidazo[1,2-a]pyridine-6-carboxylate In a flame-dried flask set under argon, a solution of ethyl 2,3-dimethyl-8-hydroxy-7-(3'-hydroxy-3'-phenylpropyl)-imidazo[1,2-a]pyridine-6-carboxylate (250 mg, 0.68 mmol) in dichloromethane (15 ml) is treated with an excess of boron trifluoride etherate (1.71 ml, 13.6 mmol). The solution is stirred for 4 hours at ambient temperature. The reaction mixture is quenched at 0° C. by addition of saturated ammonium chloride solution (20 ml). The pH is adjusted to 7 using 6 N sodium hydroxide solution (3 ml). The aqueous phase is extracted with dichloromethane (3×20 ml). The combined organic phases are washed with 20 ml of water and dried over sodium sulfate. After evaporation of the solvent the residue (245 mg of a colourless solid) is purified by flash chromatography [silica gel, solvent system: petrol ether/ethyl acetate=1:1 (v/v)]. The title compound (164 mg, 69%) is obtained as a colourless solid (melting point 146–147° C.); 99.1% purity according to HPLC analysis.

3. 2,3-Dimethyl-9-phenyl-7H-8,9-dihydro-pyrano[2,3-c]-imidazo[1,2-a]pyridine-6-(N,N-dimethyl)carbamide In a flask filled with argon, 2,3-dimethyl-8-hydroxy-7-(3'-hydroxy-3'-phenylpropyl)-imidazo[1,2-a]pyridine-6N,N-dimethyl)carbamide (2.00 g, 5.4 mmol) is dissolved in absolute dichloromethane (200 ml). The solution is stirred at ambient temperature and boron trifluoride etherate (1.4 ml, 11 mmol) is added. Gradually, a colourless precipitate is formed coating the wall of the flask. Further portions of boron trifluoride etherate are added after a reaction time of 1 hour (2.8 ml, 22 mmol) and 2 hours (1.4 ml, 11 mmol). After a total reaction time of 5 hours the supernatant solution is poured on cooled saturated ammonium chloride solution (10 ml). The resulting mixture is neutralized at 0° C. with 2 N sodium hydroxide solution. The phases are separated and the aqueous phase Is extracted with dichloromethane (3×20 ml). The combined organic phases are washed with water (20 ml) and concentrated by rotevaporation. The remaining solid (800 mg) is washed with acetone (15 ml) and diethyl ether. The title compound (0.46 g, 24%) is obtained as a colourless solid, melting point 245–247° C.; pure by means of $^1$H NMR spectroscopy and HPLC (99.6%).

Starting Materials

A. 6,8-Dibromo-2,3-dimethylimidazo[1,2-a]pyridine

A mixture of 31.8 g of 2-amino-3,5-dibromopyridine, 22 g of 3-bromo-2-butanone and 350 ml of tetrahydrofuran is heated at reflux for 9 days and the resulting precipitate is filtered off and dried under reduced pressure. The precipitate is then suspended in 1 l of water, and the suspension is adjusted to pH 8 using 6 M aqueous sodium hydroxide solution. The resulting precipitate is filtered off and washed with water. This gives 28 g of the title compound of m.p. above 90° C. (sinters).

B. 8-Benzyloxy-6-bromo-2,3-dimethylimidazo[1,2-a]pyridine

With ice-cooling, 34.8 ml of benzyl alcohol are added dropwise to a suspension of 13.5 g of sodium hydride (60% suspension in paraffin) in 510 ml of dimethylformamide, and the mixture is stirred for 1 h until the evolution of gas has ceased. 51.2 g of 6,8-dibromo-2,3-dimethylimidazo[1,2-a]pyridine are then introduced in small portions, and the mixture is stirred at room temperature for 40 h. The mixture is then poured into 1 l of ice-water and extracted three times with in each case 100 ml of dichloromethane, the combined organic extracts are washed with saturated aqueous ammonium chloride solution and twice with water and concentrated to dryness under reduced pressure, and the residue is triturated with a little ethyl acetate. The resulting precipitate is filtered off and dried under reduced pressure. This gives 43.2 g of the title compound of m.p. 151–3° C. (ethyl acetate).

C. 2,3-Dimethyl-8-benzyloxy-N-(diethyl)imidazo[1,2-a]pyridine-6-carboxamide 7.50 g (22.6 mmol) of 8-benzyloxy-6-bromo-2,3-dimethylimidazo[1,2-a]pyridine, 0.75 g (3.34 mmol) of palladium-II acetate, 2.63 g (10.02 mmol) of triphenylphosphine and 7.50 ml (53.81 mmol) of triethylamine are suspended in diethylamine (120 ml) and, at 120° C. and under a CO pressure of 6 bar, stirred in an autoclave for 16 h. After cooling, the catalyst is filtered off and the crude product is concentrated under reduced pressure and then separated and purified by column chromatography (dichloromethane/methanol: 100/1). This gives 5.58 g (15.88 mmol/70%) of the title compound as colorless crystals of m.p. 146–148° C. (acetone/diethyl ether).

D. 2,3-Dimethyl-8-hydroxy-N-(diethyl)imidazo[1,2-a]pyridine-6-carboxamide

At 78° C., 4.30 g (12.2 mmol) of 2,3-dimethyl-8-benzyloxy-N-(diethyl)imidazo[1,2-a]pyridine-6-carboxamide, 5.00 ml (54.0 mmol) of cyclohexa-1,4-diene and 0.43 g (4.04 mmol) of palladium (10% on carbon) are stirred in ethanol (43 ml) for 4 h. The catalyst is then filtered off and the concentrated residue is triturated with acetone. This gives 2.50 g (9.57 mmol/78%) of the title compound as colorless crystals of m.p. 215–218° C. (acetone/decomposition).

E. 2,3-Dimethyl-7-dimethylaminomethyl-8-hydroxy-N-(diethyl)imidazo[1,2-a]pyridine-6-carboxamide With stirring, 1.75 g (9.26 mmol) of N,N-dimethylmethyleneammonium iodide are added a little at a time to a solution of 2.20 g (8.42 mmol) of 2,3-dimethyl-8-hydroxy-N-(diethyl)-imidazo[1,2-a]pyridine-6-carboxamide in dichloromethane (100 ml). The mixture is stirred for another 16 h, and the reaction is then stopped by addition of sodium bicarbonate. The mixture is then extracted repeatedly with dichloromethane. The combined organic phases are washed with a little water and concentrated under reduced pressure. This gives 2.60 g (8.17 mmol/97%) of the title compound as a colorless foam. $^1$H-NMR (200 MHz, [d$_8$]-DMSO): δ=1.13 (t, 6H). 2.32 (s, 3 H), 2.37 (s, 3 H), 3.41 (m, 4 H), 6.38 (d, 1 H), 7.74 (d, 1 H).

F. 2,3-Dimethyl-8-hydroxy-7-((3-phenyl-3-oxo)propanyl)-N-(diethyl)imidazo[1,2-a]pyridine-6-carboxamide At 80° C., 2.40 g (7.50 mmol) of 2,3-dimethyl-7-dimethylaminomethyl-8-hydroxy-N-(diethyl)imidazo[1,2-a]pyridine-6-carboxamide, dissolved in toluene, (35.0 ml), are added dropwise with stirring to a solution of 4.50 g (10.0 mmol) of 1-phenyl-1-N-morpholinoethylene in toluene (35.0 ml) and the mixture is then stirred at 90° C. for another 1 h. The cooled reaction mixture is concentrated under reduced pressure and the crude product is separated and purified by column chromatography (dichloromethane/methanol: 13/1). This gives 1.60 g (4.07 mmol/54%) of the title compound as colorless crystals of m.p. 218–220° C. (acetone/decomposition).

G. 2,3-Dimethyl-8-hydroxy-7-((3-phenyl-3-hydroxy)propanyl)-N-(diethyl)imidazo[1,2-a]-pyridine-6-carboxamide 0.31 g (8.20 mmol) of sodium borohydride is added a little at a time and with stirring to 1.40 g (3.55 mmol) of 2,3-dimethyl-8-hydroxy-7-((3-phenyl-3-oxo)propanyl)-N-(diethyl)imidazo[1,2-a]pyridine-6-carboxamide dissolved in dichloromethane (30 ml). The reaction mixture is stirred for another 30 min and then concentrated under reduced pressure, and saturated ammonium chloride solution is added. The mixture is then extracted repeatedly with dichloromethane. The combined organic phases are concentrated under reduced pressure. The resulting crude product is separated and purified by column chromatography (dichloromethane/methanol: 13/1). This gives 1.23 g (3.10 mmol/88%) of the title compound as colorless crystals of m.p. 210–213° C. (dichloromethane/decomposition).

H. Ethyl 8-O-benzyl-2,3-dimethyl-imidazo[1,2-a]pyridine-6-carboxylate

In a Teflon-coated steel autoclave 8-benzyloxy-6-bromo-2,3-dimethylimidazo[1,2-a]pyridine (4.0 g, 12 mmol), palladium acetate (400 mg, 1.78 mmol), triphenylphosphine (1.33 g, 5.1 mmol), and triethylamine (10 ml) are dissolved in ethanol (50 ml). The autoclave is purged with carbon monoxide, pressurized to 5 bar, and heated to 100° C. for 16 hours. The reaction mixture is concentrated by rotevaporation and purified by flash chromatography (silica gel, solvent system: ethyl acetate). The crystalline solid is further purified by washing with diethyl ether. Colourless needles of the title compound (2.37 g, 61%) are obtained which show a melting point of 140–141° C. Concentration of the mother liquor yields further 1.1 g (28%) of the title compound.

I. Ethyl 2,3-dimethyl-8-hydroxy-imidazo[1,2-a]pyridine-6-carboxylate

In an inert atmosphere, ethyl 8-O-benzyl-2,3-dimethyl-imidazo[1,2-a]pyridine-6-carboxylate (8.14 g, 25.1 mmol) is dissolved in 80 ml of ethanol. The solution is treated with 1,4-cyclohexadiene (11.9 ml, 126 mmol) and 10% palladium on charcoal (0.8 g). The reaction mixture is heated to 80° C. and stirred at this temperature for 18 hours. The solution is cooled to ambient temperature, 10 g of silica gel are added, and the solvent is evaporated. The residue is added on a column filled with silica gel. Elution with a mixture of dichloromethane and methanol [15:1 (v/v)] yields the title compound (4.73 g, 80%); pure by means of $^1$H NMR spectroscopy. The colourless solid shows a melting point of 241° C. (decomp.).

J. Ethyl 2,3-dimethyl-7-(N,N-dimethylaminomethyl)-8-hydroxy-imidazo[1,2-a]pyridine-6-carboxylate Over a period of 30 minutes, N,N-dimethylmethyleneammonium iodide (Eschenmoser's salt, 435 mg, 2.35 mmol) is added to a solution of ethyl 2,3-dimethyl-8-hydroxy-imidazo[1,2-a]pyridine-6-carboxylate (500 mg, 2.14 mmol) in 15 ml of dichloromethane. The reaction mixture is stirred for 2.5 hours at ambient temperature and the formation of a colourless precipitate is observed. 20 ml portions of saturated sodium hydrogencarbonate solution and dichloromethane are added to the reaction mixture. The aqueous phase is extracted with dichloromethane (3×20 ml). The combined organic phases are washed with water (20 ml), dried over sodium sulfate, and evaporated to dryness. The title compound (578 mg, 93%) is isolated as a greenish foam containing traces of impurities.—$^1$H NMR (CDCl$_3$, 200 MHz): □=1.41 (t, 3 H), 2.40 (s, 12 H), 4.19 (s, 2 H), 4.37 (q, 2 H), 8.04 (s, 1 H).

K. Ethyl 2,3-dimethyl-8-hydroxy-7-(3'-oxo-3'-phenylpropyl)-imidazo[1,2-a]pyridine-6-carboxylate In a flame-dried flask under argon, ethyl 2,3-dimethyl-7-(N,N-dimethylaminomethyl)-8-hydroxy-imidazo[1,2-a]pyridine-6-carb-oxylate (1.17 g, 4.0 mmol) and pyrrolidine enamine (1.06 g, 5.2 mmol, preparation according to W. A. White, H. Weingarten, *J. Org. Chem.* 1967, 32, 213–214) are dissolved in absolute toluene (20 ml). The solution is heated to 100° C. After 40 minutes the reaction mixture is evaporated to dryness. The crude product (1.89 g of a red solid) is purified by flash chromatography [silica gel, solvent system: dichloromethane/methanol=15:1 (v/v)]. The title compound (1.23 g, 84%) is obtained as a brownish foam (90% purity according to $^1$H NMR analysis).—$^1$H NMR (CDCl$_3$, 200 MHz): □=1.39 (t, 3 H), 2.39 (s, 6 H), 3.46 (m$_c$, 4 H), 4.39 (q, 2 H), 7.46 (m$_c$, 3 H), 8.03 (d, 2 H), 8.10 (s, 1 H).

L. Ethyl 2,3-dimethyl-8-hydroxy-7-(3'-hydroxy-3'-phenylpropyl)-imidazo[1,2-a]pyridine-6-carboxylate A solution of ethyl 2,3-dimethyl-8-hydroxy-7-(3'-oxo-3'-phenylpropyl)-imidazo[1,2-a]pyridine-6-carboxylate (714 mg, 1.95 mmol) in ethanol (20 ml) is treated with sodium borohydride (74 mg, 1.95 mmol). The reaction mixture is stirred for 2.75 hours at ambient temperature. At 0° C. saturated ammonium chloride solution (20 ml) is added. The solution is evaporated until most of the ethanol has been removed and is extracted with dichloromethane (3×20 ml). The combined organic phases are dried over sodium sulfate and are evaporated to dryness. A brownish foam (692 mg) is obtained which is purified by flash chromatography [silica gel, solvent system: dichloromethane/methanol=15:1 (v/v)]. The title compound (540 mg, 75%) is isolated as an almost colourless foam, 90% purity according to $^1$H NMR analysis.—$^1$H NMR (CDCl$_3$, 200 MHz): □=1.40 (t, 3 H), 2.13 (m$_c$, 2 H), 2.40 (s, 3 H), 2.52 (s, 3 H), 3.26 (m$_c$, 1 H), 3.50 (m$_c$, 1H), 4.39 (q, 2 H), 4.61 (dd, 1 H), 7.24 (m$_c$, 5 H), 7.95 (s, 1 H).

M. 8-O-Benzyl-2,3-dimethyl-imidazo[1,2-a]pyridine-6-(N,N-dimethyl)carbamide

8-Benzyloxy-6-bromo-2,3-dimethylimidazo[1,2-a]pyridine (13.5 g, 40 mmol), dimethyl amine (2 M solution in THF, 200 ml, 400 mmol), palladium acetate (1.4 g, 6 mmol), and triphenylphosphine (6.2 g, 23 mmol) are added into an autoclave. The system is pressurized with carbon monoxide (6 bar) and is heated to 120° C. for 20 hours. The yellow-brown solution is concentrated by rotevaporation. 100 ml portions of water and dichloromethane are added to the residue. The aqueous phase is extracted with dichloromethane (3×20 ml). The combined organic phases are washed with water (2×20 ml) and evaporated to dryness. The crude product is purified by flash chromatography (silica gel, solvent system: dichloromethane). The title compound is isolated as a yellow-brown solid, melting point 160–161° C. Traces of impurities are visible in the $^1$H NMR spectrum.

N. 2,3-Dimethyl-8-hydroxy-imidazo[1,2-a]pyridine-6-(N,N-dimethyl)carbamide

In an inert atmosphere, 8-O-benzyl-2,3-dimethyl-imidazo[1,2-a]pyridine-6-(N,N-dimethyl)carbamide (13.0 g, 40 mmol) is dissolved in 200 ml of ethanol. The solution is treated with 1,4-cyclohexadiene (30.0 ml, 317 mmol) and 10% palladium on charcoal (1.3 g). The reaction mixture is heated to 80° C. and stirred at this temperature for 3 hours. Another portion of palladium catalyst (500 mg) and 1,4-cyclohexadiene (10 ml, 106 mmol) is added and the solution is refluxed for 18 hours. The reaction mixture is cooled to ambient temperature and the precipitate is dissolved by addition of dichloromethane (150 ml). The catalyst is removed by filtration and the filtrate is concentrated by rotevaporation. The yellow residue is washed with acetone and diethyl ether and dried. The title compound (6.2 g, 66%)

is obtained as a spectroscopically pure colourless solid.—¹H NMR (DMSO-d₆, 200 MHz): δ=2.31 (s, 3 H), 2.37 (s, 3 H), 2.99 (s, 6 H), 6.42 (d, 1 H), 7.80 (d, 1 H).

O. 2,3-Dimethyl-7N,N-dimethylaminomethyl)-8-hydroxy-imidazo[1,2-a]pyridine-6-(N,N-dimethyl)carbamide Over a period of 30 minutes, N,N-dimethylmethyleneammonium iodide (Eschenmoser's salt, 5.6 g, 30 mmol) is added to a solution of 2,3-dimethyl-8-hydroxy-imidazo[1,2-a]pyridine-6-(N,N-dimethyl)carbamide (5.5 g, 24 mmol) in 100 ml of dichloromethane. The reaction mixture is stirred for 70 minutes at ambient temperature and the formation of a yellow precipitate is observed. It is then poured on 50 ml of cooled saturated sodium hydrogencarbonate solution. The aqueous phase is extracted with dichloromethane (6×20 ml). The combined organic phases are washed with water (30 ml), dried over sodium sulfate, and evaporated to dryness. The title compound (6.5 g, 95%) is isolated as a spectroscopically pure colourless solid, melting point 210° C. (decomp.).

P. 2,3-Dimethyl-8-hydroxy-7-(3'-oxo-3'-phenylpropyl)-imidazo[1,2-a]pyridine-6-(N,N-dimethyl)carbamide In a flame-dried flask under argon, 2,3-dimethyl-7-(N,N-dimethylaminomethyl)-8-hydroxy-imidazo[1,2-a]pyridine-6-(N,N-dimethyl)carbamide (3.2 g, 11 mmol) and pyrrolidine enamine (3.1 g, 18 mmol, preparation according to W. A. White, H. Weingarten, *J. Org. Chem.* 1967, 32, 213–214) are dissolved in absolute toluene (50 ml). The solution is heated to 105° C. After 15 minutes the reaction mixture is cooled to 0° C. and poured on a mixture of ice water (50 ml) and dichloromethane (50 ml). The brown organic phase is removed and the aqueous phase is extracted with dichloromethane. The combined organic phases are washed with water (20 ml), dried over sodium sulfate, and evaporated to dryness. The crude product (5 g of a brown solid) is purified by flash chromatography [silica gel, solvent system: dichloromethane]. The title compound (3.2 g, 79%) is obtained as a brownish foam. Traces of impurities are visible in the ¹H NMR spectrum of this compound.—¹H NMR (DMSO-d₈, 200 MHz): δ=2.32 (s, 3 H), 2.36 (s, 3 H), 2.82 ($m_c$, 2 H), 2.89 (s, 3 H), 3.01 (s, 3 H), 3.21 ($m_c$, 2 H), 7.59 ($m_c$, 3 H), 7.95 (d, 2 H), 7.99 (s, 1 H).

Q. 2,3-Dimethyl-8-hydroxy-7-(3'-hydroxy-3'-phenylpropyl)-imidazo[1,2-a]pyridine-6-(N,N-dimethyl)carbamide Over a period of 20 minutes, sodium borohydride (0.40 g, 10.6 mmol) is added to a solution of 2,3-dimethyl-8-hydroxy-7-(3'-oxo-3'-phenylpropyl)-imidazo[1,2-a]pyridine-6-(N,N-dimethyl)carbamide (3.10 g, 8.5 mmol) in methanol (30 ml). The reaction mixture is stirred for 40 minutes at ambient temperature. Another portion of sodium borohydride (0.10 g, 2.6 mmol) is added and the solution is stirred for another 30 min. The reaction mixture is then poured on a mixture of saturated ammonium chloride solution (50 ml), ice (20 g), and dichloromethane (100 ml). The phases are separated and the aqueous phase is extracted with dichloromethane (3×20 ml). The combined organic phases are washed with saturated ammonium chloride solution (2×20 ml) and water (2×20 ml), dried over sodium sulfate, and evaporated to dryness. The residue is treated with acetone (12 ml). A colourless precipitate is formed which is washed with acetone and diethylether and dried. The title compound (2.10 g, 67%) is isolated as a colourless solid (m.p. 148–150° C.); pure by means of ¹H NMR spectroscopy. The mother liquor (0.8 g) is purified by flash chromatography. [silica gel, solvent system: dichloromethane/isopropanol=20:1 (v/v)] yielding another 0.29 g (9%) of the title compound.

Commercial Utility

The compounds of the formula 1 and their salts have valuable pharmacological properties which make them commercially utilizable. In particular, they exhibit marked inhibition of gastric acid secretion and an excellent gastric and intestinal protective action in warm-blooded animals, in particular humans. In this connection, the compounds according to the invention are distinguished by a high selectivity of action, an advantageous duration of action, a particularly good enteral activity, the absence of significant side effects and a large therapeutic range.

"Gastric and intestinal protection" in this connection is understood as meaning the prevention and treatment of gastrointestinal diseases, in particular of gastrointestinal inflammatory diseases and lesions (such as, for example, gastric ulcer, duodenal ulcer, gastritis, hyperacidic or medicament-related functional dyspepsia), which can be caused, for example, by microorganisms (e.g. *Helicobacter pylori*), bacterial toxins, medicaments (e.g. certain antiinflammatories and antirheumatics), chemicals (e.g. ethanol), gastric acid or stress situations.

In their excellent properties, the compounds according to the invention surprisingly prove to be clearly superior to the compounds known from the prior art in various models in which the antiulcerogenic and the antisecretory properties are determined. On account of these properties, the compounds of the formula 1 and their pharmacologically acceptable salts are outstandingly suitable for use in human and veterinary medicine, where they are used, in particular, for the treatment and/or prophylaxis of disorders of the stomach and/or intestine.

A further subject of the invention are therefore the compounds according to the invention for use in the treatment and/or prophylaxis of the abovementioned diseases.

The invention likewise includes the use of the compounds according to the invention for the production of medicaments which are employed for the treatment and/or prophylaxis of the above-mentioned diseases.

The invention furthermore includes the use of the compounds according to the invention for the treatment and/or prophylaxis of the abovementioned diseases.

A further subject of the invention are medicaments which comprise one or more compounds of the formula 1 and/or their pharmacologically acceptable salts.

The medicaments are prepared by processes which are known per se and familiar to the person skilled in the art. As medicaments, the pharmacologically active compounds according to the invention (=active compounds) are either employed as such, or preferably in combination with suitable pharmaceutical auxiliaries or excipients in the form of tablets, coated tablets, capsules, suppositories, patches (e.g. as TTS), emulsions, suspensions or solutions, the active compound content advantageously being between 0.1 and 95% and it being possible to obtain a pharmaceutical administration form exactly adapted to the active compound and/or to the desired onset and/or duration of action (e.g. a sustained-release form or an enteric form) by means of the appropriate selection of the auxiliaries and excipients.

The auxiliaries and excipients which are suitable for the desired pharmaceutical formulations are known to the person skilled in the art on the basis of his/her expert knowledge. In addition to solvents, gel-forming agents, suppository bases, tablet auxiliaries and other active compound excipients, it is possible to use, for example, antioxidants, dispersants, emulsifiers, antifoams, flavor corrigents, preservatives, solubilizers, colorants or, in particular, permeation promoters and complexing agents (e.g. cyclodextrins).

The active compounds can be administered orally, parenterally or percutaneously.

In general, it has proven advantageous in human medicine to administer the active compound(s) in the case of oral administration in a daily dose of approximately 0.01 to approximately 20, preferably 0.05 to 5, in particular 0.1 to 1.5, mg/kg of body weight, if appropriate in the form of several, preferably 1 to 4, individual doses to achieve the desired result. In the case of a parenteral treatment, similar or (in particular in the case of the intravenous administration of the active compounds), as a rule, lower doses can be used. The establishment of the optimal dose and manner of administration of the active compounds necessary in each case can easily be carried out by any person skilled in the art on the basis of his/her expert knowledge.

If the compounds according to the invention and/or their salts are to be used for the treatment of the abovementioned diseases, the pharmaceutical preparations can also contain one or more pharmacologically active constituents of other groups of medicaments, for example: tranquillizers (for example from the group of the benzodiazepines, for example diazepam), spasmolytics (for example, bietamiverine or camylofine), anticholinergics (for example, oxyphencyclimine or phencarbamide), local anesthetics, (for example, tetracaine or procaine), and, if appropriate, also enzymes, vitamins or amino acids.

To be emphasized in this connection is in particular the combination of the compounds according to the invention with pharmaceuticals which inhibit acid secretion, such as, for example, $H_2$ blockers (e.g. cimetidine, ranitidine), $H^+/K^+$ ATPase inhibitors (e.g. omeprazole, pantoprazole), or further with so-called peripheral anticholinergics (e.g. pirenzepine, telenzepine) and with gastrin antagonists with the aim of increasing the principal action in an additive or super-additive sense and/or of eliminating or of decreasing the side effects, or further the combination with antibacterially active substances (such as, for example, cephalosporins, tetracyclines, penicillins, macrolides, nitroimidazoles or alternatively bismuth salts) for the control of *Helicobacter pylori*. Suitable antibacterial co-components which may be mentioned are, for example, mezlocillin, ampicillin, amoxicillin, cefalothin, cefoxitin, cefotaxime, imipenem, gentamycin, amikacin, erythromycin, ciprofloxacin, metronidazole, clarithromycin, azithromycin and combinations thereof (for example clarithromycin+metronidazole).

Pharmacology

The excellent gastric protective action and the gastric acid secretion-inhibiting action of the compounds according to the invention can be demonstrated in investigations on animal experimental models. The compounds according to the invention investigated in the model mentioned below have been provided with numbers which correspond to the numbers of these compounds in the examples.

Testing of the Secretion-Inhibiting Action on the Perfused Rat Stomach

In Table A which follows, the influence of the compounds according to the invention on the pentagastrin-stimulated acid secretion of the perfused rat stomach after intraduodenal administration in vivo is shown.

TABLE A

| No. | Dose (μmol/kg) i.d. | Inhibition of acid secretion (%) |
|---|---|---|
| 1 | 3.0 | 100 |
| 2 | 3.0 | 100 |
| 3 | 3.0 | 100 |

Methodology

The abdomen of anesthetized rats (CD rat, female, 200–250 g; 1.5 g/kg i.m. urethane) was opened after tracheotomy by a median upper abdominal incision and a PVC catheter was fixed transorally in the esophagus and another via the pylorus such that the ends of the tubes just projected into the gastric lumen. The catheter leading from the pylorus led outward into the right abdominal wall through a side opening.

After thorough rinsing (about 50–100 ml), warm (37° C.) physiological NaCl solution was continuously passed through the stomach (0.5 ml/min, pH 6.8–6.9; Braun-Unita I). The pH (pH meter 632, glass electrode EA 147; $\phi=5$ mm, Metrohm) and, by titration with a freshly prepared 0.01N NaOH solution to pH 7 (Dosimat 665 Metrohm), the secreted HCl were determined in the effluent in each case collected at an interval of 15 minutes.

The gastric secretion was stimulated by continuous infusion of 1 μg/kg (=1.65 ml/h) of i.v. pentagastrin (left femoral vein) about 30 min after the end of the operation (i.e. after determination of 2 preliminary fractions). The substances to be tested were administered intraduodenally in a 2.5 ml/kg liquid volume 60 min after the start of the continuous pentagastrin infusion.

The body temperature of the animals was kept at a constant 37.8–38° C. by infrared irradiation and heat pads (automatic, stepless control by means of a rectal temperature sensor).

What is claimed is:
1. A compound of the formula I

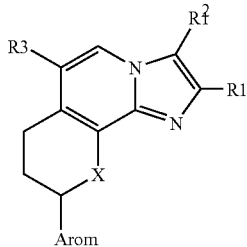

(1)

where
R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl,
R2 is hydrogen, 1–4C-alkyl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl,
R3 is hydroxy-1–4C-alkyl, 1–4C-alkoxy-1–4C-alkyl, 1–4C-alkoxy-1–4C-alkoxy-1–4C-alkyl, 1–4C-alkoxycarbonyl, fluoro-1–4C-alkoxy-1–4C-alkyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy-1–4C-alkyl or 1–4C-alkoxy-1–4C-alkyl,
or where
R31 and R32 together and including the nitrogen atom to which they are attached form a pyrrolidino, piperidino or morpholino radical,
Arom is a R4-, R5-, R6- and R7-substituted mono- or bicyclic aromatic radical selected from the group consisting of phenyl, naphthyl, pyrrolyl, pyrazolyl, imidazolyl, 1,2,3-triazolyl, indolyl, benzimidazolyl, furanyl, benzofuranyl, thiophenyl benzothiophenyl, thiazolyl, isoxazolyl, pyridinyl, pyrimidinyl, quinolinyl and isoquinolinyl,
where
R4 is hydrogen, 1–4C-alkyl, hydroxy-1–4C-alkyl, 1–4C-alkoxy, 2–4C-alkenyloxy, 1–4C-alkylcarbonyl, carboxyl, 1–4C-alkoxycarbonyl, carboxy-1–4C-alkyl, 1–4C-alkoxycarbonyl-1–4C-alkyl, halogen, hydroxyl, aryl, aryl-1–4C-alkyl, aryloxy, aryl-1–4C-alkoxy, trifluoromethyl, nitro, amino, mono- or di-1–4C-alkylamino, 1–4C-alkylcarbonylamino, 1–4C-alkoxycarbonylamino, 1–4C-alkoxy-1–4C-alkoxycarbonylamino or sulfonyl,
R5 is hydrogen, 1–4C-alkyl, 1–4C-alkoxy, 1–4C-alkoxycarbonyl, halogen, trifluoromethyl or hydroxyl,
R6 is hydrogen, 1–4C-alkyl or halogen and
R7 is hydrogen, 1–4C-alkyl or halogen,
where
aryl is phenyl or substituted phenyl having one, two or three identical or different substituents from the group consisting of 1–4C-alkyl, 1–4C-alkoxy, carboxyl, 1–4C-alkoxycarbonyl, halogen, trifluoromethyl, nitro, trifluoromethoxy, hydroxyl and cyano,
X is O or NH,
or a salt, hydrate, hydrate of a salt, solvate or solvate of a salt thereof.

2. A compound of the formula 1 as claimed in claim 1, where
R1 is hydrogen, 1–4C-alkyl, 3–7C-cycloalkyl, 1–4C-alkoxy-1–4C-alkyl, 2–4C-alkynyl or fluorol-1–4C-alkyl,
R2 is hydrogen, 1–4C-alkyl, halogen, 2–4C-alkenyl, 2–4C-alkynyl or fluoro-1–4C-alkyl,
R3 is hydroxy-1–4C-alkyl, 1–4C-alkoxy-1–4C-alkyl, 1–4C-alkoxyl-1–4C-alkoxy-1–4C-alkyl, 1–4C-alkoxycarbonyl or the radical —CO—NR31R32,
where
R31 is hydrogen, 1–7C-alkyl, hydroxy-1–4C-alkyl or 1–4C-alkoxy-1–4C-alkyl and
R32 is hydrogen, 1–7C-alkyl, hydroxy1–4C-alkyl or 1–4C-alkoxy-1–4C-alkyl,
or where
R31 and R32 together and including the nitrogen atom to which they are attached are a pyrrolidino, piperidino or morpholino radical,
Arom is a R4-, R5-, R6- and R7-substituted mono- or bicyclic aromatic radical selected from the group consisting of phenyl, furanyl and thiophenyl,
where
R4 is hydrogen, 1–4C-alkyl, hydroxy-1–4C-alkyl, 1–4C-alkoxy, 1–4C-alkylcarbonyl, carboxyl, 1–4C-alkoxycarbonyl, halogen, hydroxyl, trifluoromethyl, 1–4C-alkylcarbonylamino, 1–4C-alkoxycarbonylamino, 1–4C-alkoxy-1–4C-alkoxycarbonylamino or sulfonyl,
R5 is hydrogen, 1–4C-alkyl, 1–4C-alkoxy, 1–4C-alkoxycarbonyl, halogen, trifluoromethyl or hydroxyl,
R6 is hydrogen or 1–4C-alkyl and
R7 is hydrogen,
X is O or NH,
or a salt, hydrate, hydrate of a salt, solvate or solvate of a salt thereof.

3. A compound of the formula 1 as claimed in claim 1, where
R1 is 1–4C-alkyl,
R2 is 1–4C-alkyl, halogen or fluoro-1–4C-alkyl,
R3 is hydroxyl-1–4C-alkyl, 1–4C-alkoxyl-1–4C-alkyl, 1–4C-alkoxy-1–4C-alkoxy-1–4C-alkyl, 1–4C-alkoxycarbonyl or the radical —CO—NR31R32,
where
R31 is hydrogen, 1–4C-alkyl, hydroxy-1–4C-alkyl or 1–4C-alkoxy-1–4C-alkyl and
R32 is 1–4C-alkyl, hydroxy-1–4C-alkyl or 1–4C-alkoxy-1–4C-alkyl,
or where
R31 and R32 together and including the nitrogen atom to which they are attached are a pyrrolidino, piperidino or morpholino radical,
Arom is R4-, R5-, R6- and R7-substituted phenyl,
where
R4 is hydrogen or 1–4C-alkyl,
R5 is hydrogen or 1–4C-alkyl,
R6 is hydrogen or 1–4C-alkyl and
R7 is hydrogen,
X is O or NH,
or a salt, hydrate, hydrate of a salt, solvate or solvate of a salt thereof.

4. A compound of the formula 1 as claimed in claim 1, where

R1 is methyl,

R2 is methyl, chlorine or difluoromethyl,

R3 is hydroxymethyl, methoxymethyl, methoxyethoxymethyl, 1–4C-alkoxycarbonyl or the radical —CO—N—R31R32, where R31 is methyl or ethyl and R32 is methyl or ethyl, or where R31 and R32 together and including the nitrogen atom to which they are attached are a morpholino radical, Arom is phenyl, 2-methylphenyl, 2-isopropylphenyl, 2,6-dimethylphenyl, 2,6-diisopropylphenyl, 2,4,6-trimethylphenyl or 2,4,6-triisopropylphenyl and X is O or NH, or a salt, hydrate, hydrate of a salt, solvate or solvate of a salt thereof.

5. A compound of the formula 1 as claimed in claim 1, where

R1 is 1–4C-alkyl,

R2 is 1–4C-alkyl,

R3 is 1–4C-alkoxycarbonyl or the radical —CO—NR31R32, where

R31 is 1–4C-alkyl and

R32 is 1–4C-alkyl,

Arom is phenyl and

X is O, or a salt, hydrate, hydrate of a salt, solvate or solvate of a salt thereof.

6. A compound of the formula 1 as claimed in claim 1, where

R1 is 1–4C-alkyl,

R2 is 1–4C-alkyl,

R3 is 1–4C-alkoxycarbonyl or the radical —CO—NR31R32, where

R31 is 1–4C-alkyl and

R32 is 1–4C-alkyl,

Arom is phenyl or 2-methyl-6-ethylphenyl and

X is O, or a salt, hydrate, hydrate of a salt, solvate or solvate of a salt thereof.

7. A pharmaceutical composition comprising a compound as claimed in claim 1 or a pharmaceutically acceptable salt, hydrate, hydrate of a salt, solvate or solvate of a salt thereof.

8. A method of inhibiting gastric acid secretion in a patient comprising administering to a patient in need thereof a therapeutically effective amount of a compound as claimed in claim 1 or a pharmaceutically acceptable salt, hydrate, hydrate of a salt, solvate or solvate of a salt thereof.

9. A compound of the formula I as claimed in claim 1, where

R1 is hydrogen, 1–4C-alkyl, 3–7C-cycloalkyl, 3–7C-cycloalkyl-1–4C-alkyl, 1–4C-alkoxy, 1–4C-alkoxy-1–4C-alkyl, 1–4C-alkoxycarbonyl, 2–4C-alkenyl, 2–4C-alkynyl, fluoro-1–4C-alkyl or hydroxy-1–4C-alkyl, R2 is hydrogen, 1–4C-alkyl, 3–7C-cycloalkyl, 3–7C-cycloalkyl-1–4C-alkyl, 1–4C-alkoxycarbonyl, hydroxy-1–4C-alkyl, halogen, 2–4C-alkenyl, 2–4C-alkynyl, fluoro-1–4C-alkyl or cyanomethyl, R3 is hydroxy-1–4C-alkyl, 1–4C-alkoxy-1–4C-alkyl, 1–4C-alkoxy-1–4C-alkoxy-1–4C-alkyl, 1–4C-alkoxycarbonyl, fluoro-1–4C-alkoxy-1–4C-alkyl or the radical —CO—NR31R32, where R31 is hydrogen, 1–7C-alkyl, hydroxy-1–4C-alkyl or 1–4C-alkoxy-1–4C-alkyl and R32 is hydrogen, 1–7C-alkyl, hydroxy-1–4C-alkyl or 1–4C-alkoxy-1–4C-alkyl, or where R31 and R32 together and including the nitrogen atom to which they are attached form a pyrrolidino, piperidino or morpholino radical, Arom is a R4-, R5-, R6- and R7-substituted mono- or bicyclic aromatic radical selected from the group consisting of phenyl, naphthyl, pyrrolyl, thiophenyl and pyridinyl, where R4 is hydrogen, 1–4C-alkyl, halogen or trifluoromethyl, R5 is hydrogen, 1–4C-alkyl, halogen or trifluoromethyl, R6 is hydrogen, 1–4C-alkyl or halogen and R7 is hydrogen, 1–4C-alkyl or halogen, X is O or NH, or a salt, hydrate, hydrate of a salt, solvate or solvate of a salt thereof.

* * * * *

UNITED STATES PATENT AND TRADEMARK OFFICE
CERTIFICATE OF CORRECTION

PATENT NO. : 7,223,771 B2
APPLICATION NO. : 10/485515
DATED : May 29, 2007
INVENTOR(S) : Buhr et al.

It is certified that error appears in the above-identified patent and that said Letters Patent is hereby corrected as shown below:

Claim 1, Column 23, Line 45,
Please delete

" thiophenyl benzothiophenyl, " and replace with

-- thiophenyl, benzothiophenyl --

Claim 2, Column 24, Lines 9-10,
Please delete

" fluorol-1-4C-alkyl, " and replace with

-- fluoro-1-4C-alkyl, --

Claim 2, Column 24, Line 14,
Please delete

" 1-4C-alkoxyl-1-4C-alkoxy-1-4C-alkyl, " and replace with

-- 1-4C-alkoxy-1-4C-alkoxy-1-4C-alkyl, --

Claim 2, Column 24, Line 19,
Please delete

" hydroxyl-4C-alkyl " and replace with

-- hydroxy-1-4C-alkyl --

UNITED STATES PATENT AND TRADEMARK OFFICE
CERTIFICATE OF CORRECTION

PATENT NO. : 7,223,771 B2
APPLICATION NO. : 10/485515
DATED : May 29, 2007
INVENTOR(S) : Buhr et al.

It is certified that error appears in the above-identified patent and that said Letters Patent is hereby corrected as shown below:

Claim 2, Column 24, Line 47,
Please delete

" hydroxyl-1-4C-alkyl, " and replace with

-- hydroxy-1-4C-alkyl, --

Claim 2, Column 24, Line 47,
Please delete

" 1-4C-alkoxyl-1-4C-alkyl, " and replace, with

-- 1-4C-alkoxy-1-4C-alkyl, --

Signed and Sealed this

Tenth Day of July, 2007

JON W. DUDAS
*Director of the United States Patent and Trademark Office*